US008681932B2

(12) United States Patent
Laukkanen

(10) Patent No.: US 8,681,932 B2
(45) Date of Patent: *Mar. 25, 2014

(54) MEDICAL COMPUTED TOMOGRAPHY IMAGING APPARATUS FOR IMAGING EXTREMITIES

(75) Inventor: Tapio Laukkanen, Espoo (FI)

(73) Assignee: Planmed Oy, Helsinki (FI)

(*) Notice: Subject to any disclaimer, the term of this patent is extended or adjusted under 35 U.S.C. 154(b) by 0 days.

This patent is subject to a terminal disclaimer.

(21) Appl. No.: 13/695,119

(22) PCT Filed: Apr. 28, 2011

(86) PCT No.: PCT/FI2011/050389
§ 371 (c)(1),
(2), (4) Date: Oct. 29, 2012

(87) PCT Pub. No.: WO2011/135188
PCT Pub. Date: Nov. 3, 2011

(65) Prior Publication Data
US 2013/0044855 A1 Feb. 21, 2013

(30) Foreign Application Priority Data

Apr. 29, 2010 (FI) .................................... 20100180
Sep. 30, 2010 (FI) .................................... 20100335

(51) Int. Cl.
H05G 1/02 (2006.01)
H05G 1/00 (2006.01)

(52) U.S. Cl.
USPC .............................. 378/20; 378/195; 378/208

(58) Field of Classification Search
USPC ........ 378/4–20, 193–198, 204, 205, 208, 210
See application file for complete search history.

(56) References Cited

U.S. PATENT DOCUMENTS

| 4,922,915 | A  | * | 5/1990 | Arnold et al. ................. 382/128 |
| 6,315,445 | B1 | * | 11/2001 | Mazess et al. ................. 378/196 |
| 7,108,421 | B2 |   | 9/2006 | Gregerson et al. |
| 7,388,941 | B2 |   | 6/2008 | Sukovic et al. |
| 2004/0022350 | A1 | * | 2/2004 | Gregerson et al. ............. 378/15 |
| 2005/0036584 | A1 |   | 2/2005 | Lebovic et al. |
| 2006/0074286 | A1 |   | 4/2006 | Miller et al. |
| 2006/0245539 | A1 | * | 11/2006 | Sukovic et al. ................. 378/20 |
| 2007/0244384 | A1 |   | 10/2007 | Gore |
| 2008/0212743 | A1 |   | 9/2008 | Gregerson et al. |

FOREIGN PATENT DOCUMENTS

| DE | 20 2004 003 840 U1 | 8/2004 |
| GB | 2 038 150 A | 7/1980 |
| JP | 2008278902 A | 11/2008 |
| WO | 0108558 A1 | 2/2001 |

* cited by examiner

Primary Examiner — Anastasia Midkiff
(74) Attorney, Agent, or Firm — Fay Sharpe LLP

(57) ABSTRACT

The invention relates to a medical computed tomography imaging apparatus for imaging extremities, which apparatus includes a support construction (1) which is arranged to support a substantially ring-shaped structure supporting imaging means (2), which imaging means include a source of radiation (21) and a receiver of image information (22), which imaging means are arranged within said substantially ring-shaped structure supporting the imaging means (2) substantially to the opposite sides of each other and to be moved inside said ring-shaped structure supporting the imaging means (2). The apparatus according to the invention is arranged with at least one padding element (15) to at least one such point whereto the patient can when positioning oneself to be imaged, in connection with the actual patient positioning and/or during the actual imaging, depending on the imaging mode in question touch, lean on, kneel, sit on or step on.

14 Claims, 4 Drawing Sheets

MEDICAL COMPUTED TOMOGRAPHY IMAGING APPARATUS FOR IMAGING EXTREMITIES

FIELD OF INVENTION

The invention relates to a medical imaging apparatus according to the preamble of claim 1.

BACKGROUND OF INVENTION

Conventional apparatuses employed in medical x-ray imaging most simple of their basic structure comprise a source of radiation which is used together with a film cassette separate from the source of radiation. Hospitals commonly use also the so-called C-arch x-ray apparatuses where the source of radiation and the receiver of image information are arranged at the opposite ends of the arched arm part. Conventionally, a device group of its own consists of large-size and extremely expensive computed tomography apparatuses where the patient is typically positioned for imaging in the recumbent position within a ring-shaped or tubular structure.

Computed tomography apparatuses have also been developed into more lightweight versions. As an example of prior art arrangements, we refer to U.S. Pat. Nos. 7,108,421 and 7,388,941. In such apparatuses, imaging means is rotatable for 360 degrees around the imaging station are arranged within a ring-shaped O-arm supported from the side. The O-arm may be arranged adjustable for its height position and turnable with respect to a horizontal axis.

As conventional computed tomography apparatuses have been quite massive and expensive, acquiring them e.g. for the use of hospital emergency rooms has not been possible in practice. On the other hand, it is also typical for commercial computed tomography apparatuses that they are not necessarily designed for imaging some specific anatomy or anatomies but they are more or less general imaging apparatuses. If e.g. desiring to image the patient's whole torso, the imaging station to be arranged to the apparatus as well as other dimensions of the apparatus have had to be implemented in respective proportions.

BRIEF DESCRIPTION OF INVENTION

The object of the present invention is to advance the state of the art concerning x-ray imaging apparatuses, especially the ones less expensive and of smaller size referred to above as compared to the conventional computed tomography apparatuses. Preferably, embodiments of the invention offer a possibility to implement a cone-beam computed tomography imaging apparatus particularly designed applicable for imaging extremities, for example, the properties and price of which could bring purchase of the apparatus within resources available for e.g. emergency clinics. As the conventional computed tomography employs a narrow fan-like beam, in cone-beam tomography the beam is collimated to be genuinely two-dimensional but often to cover only a quite small specific area (volume) of the object being imaged. A special object of the invention is to advance development particularly in the field of x-ray imaging apparatuses comprising a ring-shaped arm part of the above-described type, the construction, characteristics and dimensions of which differ in many respects from the conventional hospital computed tomography apparatuses and in which the patient is positioned for imaging in another way than in conventional computed tomography apparatuses, whereto the patient is positioned lying on an imaging tray.

Especially, the object of the invention is an arrangement which can, depending on the imaging mode in question, either facilitate the patient to position oneself to be imaged, the patient positioning itself and/or the actual imaging event.

Essential characteristics of the invention are described in the accompanying patent claims. Especially essential for the invention is a padding arranged to at least one such point of the apparatus which, depending on the imaging mode in question, the patient can touch, lean on, sit on or step on either when positioning oneself to be imaged, in connection with the actual patient positioning and/or during the actual imaging.

Next, the invention and its preferable embodiments will be described in more detail also with reference to the enclosed figures.

DETAILED DESCRIPTION OF INVENTION

In the following, the terms centre and central axis will be used in connection with structures which do not necessarily form a true, full circle but are of circular shape only for their prevailing part. To avoid ambiguity, these terms refer in connection with this specification to a point and an axis which would be the centre or central axis of the structure in question in case that structure would form a full circle.

Furthermore, concerning one component of the apparatus according to the invention, this specification employs terms a substantially ring-shaped structure and an O-arm. When the dimension in the direction of the central axis of this structure can be significantly large with respect to the diameter of the ring-shaped structure in question, for the avoidance of doubt it is stated that in the following, vertical position of the O-arm refers to a position where the central axis of the O-arm is horizontally oriented and horizontal position of the O-arm refers to a position where its central axis is vertically oriented.

Figure 1:
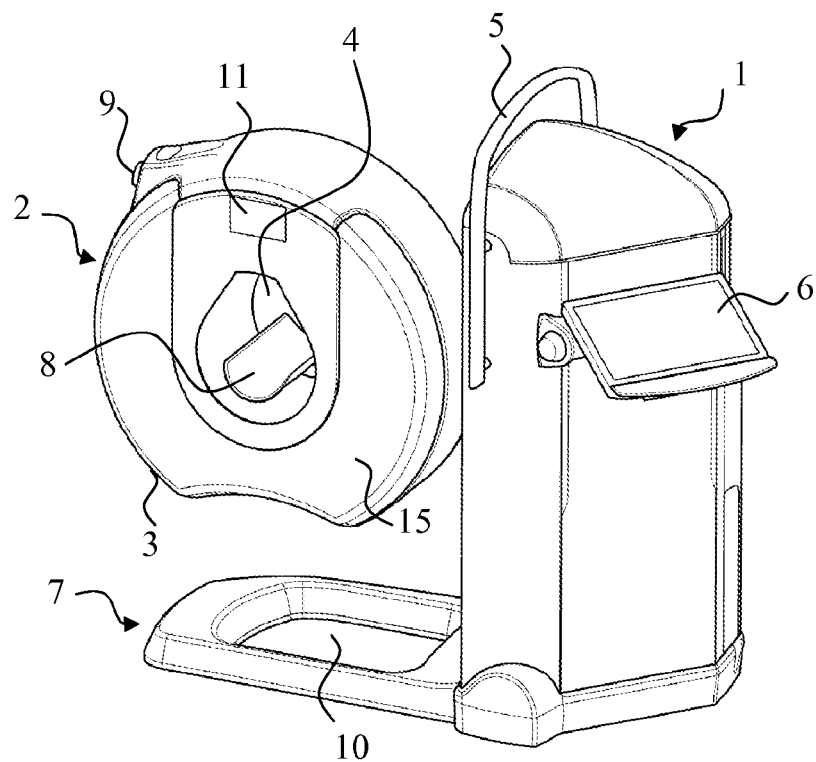
FIG. 1 shows a general view of one imaging apparatus according to the invention, its basic structure including a support construction and a substantially ring-shaped O-arm.

FIG. 1 shows a general view of one imaging apparatus according to the invention. The basic structure of the apparatus includes a support construction (1) which supports a substantially ring-shaped structure (2) within which imaging means (21, 22) of the apparatus are located and which is also referred to as an O-arm in this context. This O-arm (2) is arranged with an examination opening (4) within which an anatomy to be imaged is positioned. FIG. 1 further shows a patient support rail (5) arranged to the support construction (1), a user interface (6) being in functional connection with a control system of the apparatus, a possibly detachably attached pedestal or base part (7) projecting substantially in the direction of the O-arm, and a positioning support (8) arranged to the examination opening (4). In a preferable embodiment according to FIG. 1, also a display screen (11) is arranged substantially on the surface of the ring-shaped structure (2), at its upper edge.

Mounting of the structure (2) supporting the imaging means to the support construction (1) can be arranged to enable adjustment of the height position of the O-arm (2). Furthermore, this O-arm (2) can be arranged to be turnable in at least one direction for at least 90 degrees from the vertical position shown in FIG. 1 to the horizontal position. The control of these manoeuvres can be arranged implementable aside from the user interface (6) being connected with the control system of the apparatus also by means of a joy stick (9) arranged into connection with the O-arm (2) and/or the support frame (1).

When looking at the cross-section perpendicular to the direction of the central axis of the O-arm (2) shown in FIG. 1, i.e. the radial cross-section of the O-arm (2), an outer cover (3) of the O-arm (2) forms for its prevailing part a circle which yet comprises a sector where the distance from the centre of said circle to the edges of the outer cover (3) is smaller than the radius of that portion being circular for its prevailing part. In the embodiment of the invention according to FIG. 1, the part in said sector being cut off the O-arm (2) is evenly curved in the opposite direction with respect to the arch of the circle of the prevailing portion of the outer cover (3), but this cut part can also be of some other shape, such as wedge-shaped, rectangular, straight or even curved in the same direction as the portion of the arch of the outer cover (3) substantially of the shape of a circle.

When a sector of the kind described above is arranged at a section of the O-arm (2) substantially orienting downwards or being orientable downwards, it can be easier to implement e.g. imaging of lower extremities in sitting position when thanks to the invention, the examination opening (4) can be driven closer to the floor level as compared to an O-arm (2) not comprising such a cut. On the other hand, if the imaging apparatus is provided with a possibility to adjust the height position of the O-arm (2) and to turn the O-arm (2) to a position where the central axis of the O-arm (2) is substantially vertical, one may use the apparatus to image the patient in a standing position, too. Then, said cut arranged to the O-arm (2) makes it easier for the patient to step into the examination opening (4) and out of the examination opening as the length of the step one needs to take over the 'doorstep' formed by the O-arm (2) will be shorter.

In the embodiment of the invention according to FIG. 1, the examination opening (4) is implemented only for its prevailing part substantially as a circle. A sector has been arranged to the examination opening (4) which forms an extension to the circle. That is, the examination opening (4) is provided with a sector in the area of which the distance of the edge of the examination opening (4) from the centre of the circular portion of the examination opening (4) (or from the central axis of the O-arm (2)) is longer than the radius of the circular portion of the examination opening (4). Such design of the examination opening (4) is preferable e.g. when the aim is to realize dimensions of the cross-section perpendicular with respect to the central axis of the O-arm structure as small as possible, such as when considering an embodiment basically designed for imaging anatomies having a smaller diameter than the diameter of the human torso, such as extremities.

Enlarging the examination opening (4) in some sector of the circle facilitates patient positioning e.g. when imaging a plastered leg. In such an embodiment of the invention we are talking about an examination opening (4) the diameter of the portion of the shape of an arch of a circle of which is e.g. of the order of 30-35 cm. In the embodiment of the invention according to FIG. 1, the examination opening (4) is substantially of the shape of a droplet, i.e. the shape of its extension is substantially an equilateral triangle having a truncated apex, but said extension can naturally be of some other shape as well.

Figure 2:
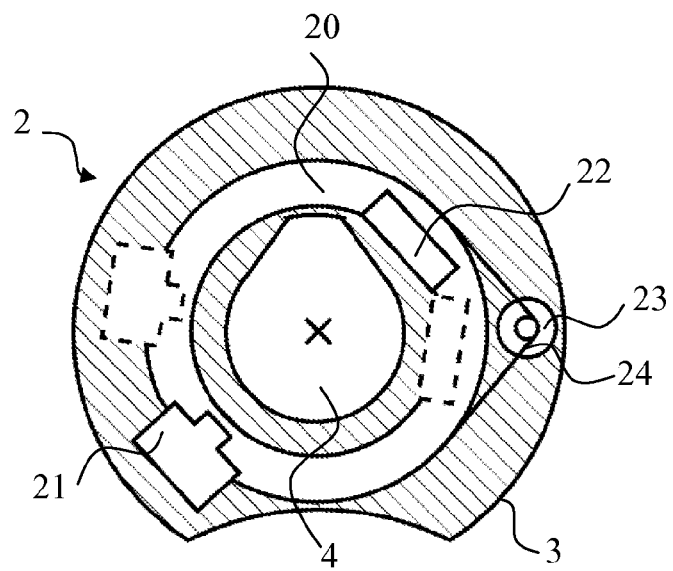
FIG. 2 shows one arrangement according to the invention for arranging imaging means to the ring-shaped imaging part.

According to the basic structure of the apparatus according to the invention, the imaging means, i.e. a source of radiation (21) and a receiver of image information (22), are arranged within the substantially ring-shaped structure (2) supporting the imaging means and as movable along a curved path within said structure, substantially on opposite sides of the examination opening (4), whereby the distance between the edge of the examination opening (4) and the outer cover (3) of the O-arm (2) (or the radial dimension of the ring of the O-arm) must naturally be arranged of adequate size to enable said paths. FIG. 2 shows a possible embodiment of the invention which includes an ring-shaped support part (20) arranged within the O-arm (2), whereto substantially on opposite sides from each other are arranged the source of radiation (21) and the receiver of image information (22). The support part (20) is arranged rotatable within the structure (2) supporting the imaging means by means of an actuator (23) and a transmission belt (24). Hence, it is possible to image the object positioned at the examination opening (4) from different directions within the range of the angle of rotation of the imaging means and to create of thus acquired image information a voxel model by means of image-data processing methods known as such.

In one preferable embodiment of the invention according to FIG. 2, the source of radiation (21) and the receiver of image information (22) are arranged movable within substantially ring-shaped structure (2) supporting the imaging means with respect to a centre of rotation such that the source of radiation (21) (the focus of the source of radiation) moves at a different distance from said centre of rotation than the receiver of image information (22). In the arrangement according to FIG. 2, the source of radiation (21) is attached on the outer circumference of the ring-shaped support part (20) whereby, when rotating the support part (20), the focus of the source of radiation (21) moves farther from said centre of rotation than the receiver of image information (22) attached on the side of the inner circumference of the support part (20). When the receiver of image information (22) is thus brought closer to the volume being imaged, it is possible when using a detector (22) of given size to use a wider beam and thus increase the volume being imageable as compared to that the receiver of image information (22) were to move farther from the object.

Figure 3:
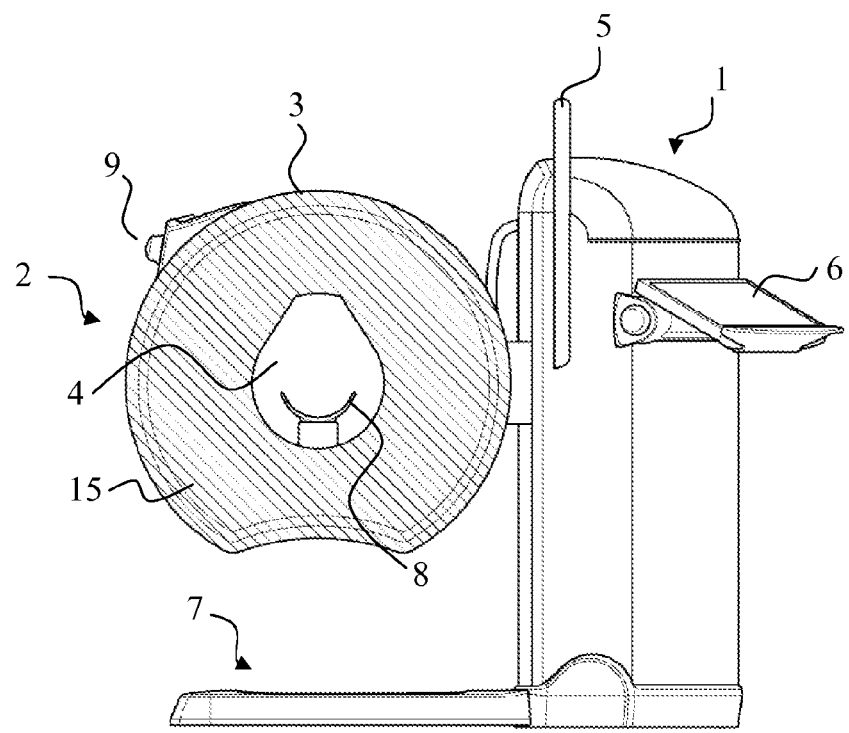
FIGS. 3-5 demonstrate different ways to arrange at least one padding element on the ring-shaped structure supporting the imaging means.
Figure 4:
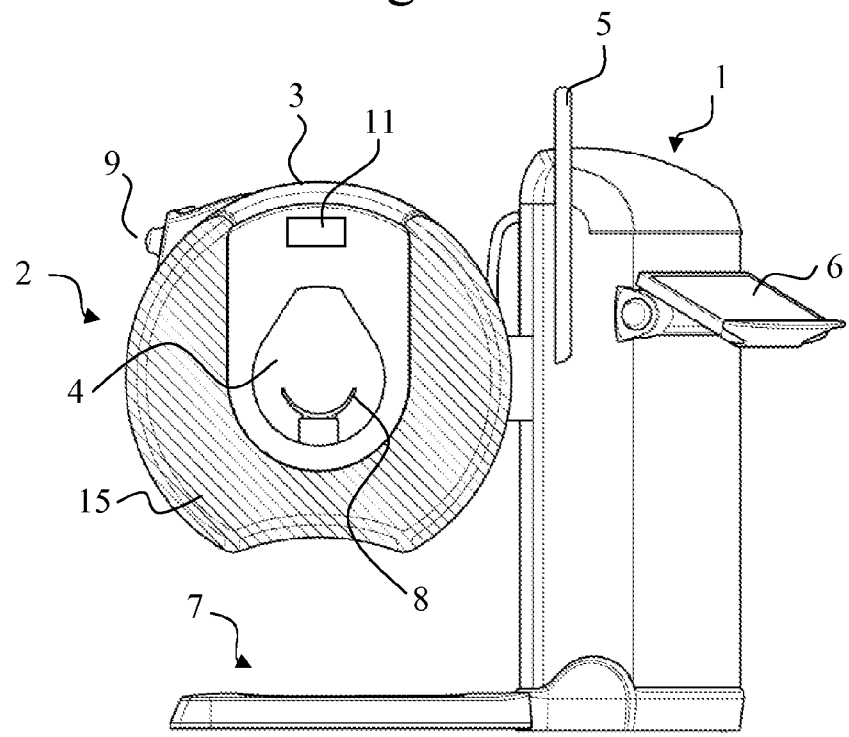
Figure 5:
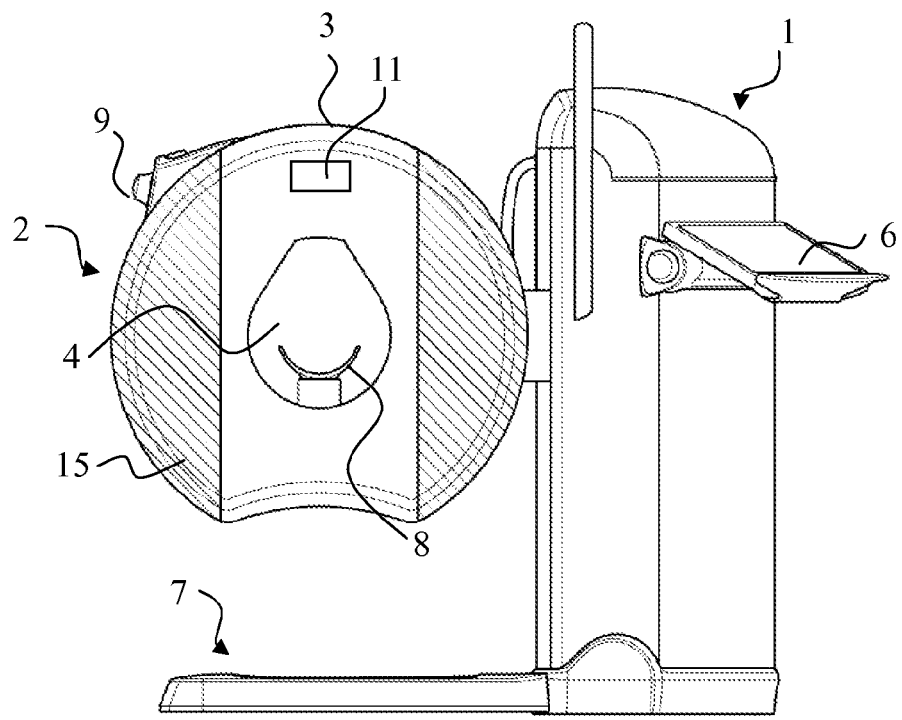

FIGS. 3-5 show how the apparatus is arranged with at least one padding element (15) on at least one such point which, depending on the imaging mode in question, the patient can touch, lean on, sit on or step on either when positioning oneself to be imaged, in connection with the actual patient positioning and/or during the actual imaging. Such padding element (15) can be arranged to the structure (2) supporting the imaging means (21, 22) either to cover substantially whole of that surface of the structure supporting the imaging means (2) from the direction of which the patient steps or positions oneself for imaging into said structure (2) supporting the imaging means (21, 22), or at least part of it. When considering the structure (2) supporting the imaging means (21, 22) at its vertical position, the area where there is no padding can be arranged to be some area within the upper section of that surface. On such area, e.g. a display screen (11) can be arranged through which the patient can be shown various information relating to the imaging event. The area without the padding (15) can also be arranged on the lower portion of the aforesaid area, as well as at the immediate proximity of the examination opening (4) of the apparatus. Again, a padding element (15) can also be arranged on the surface of the support construction (1) the normal of which points towards the structure (2) supporting the imaging means (21, 22).

Preferably at least one padding element (15) is arranged detachably attached. The padding (15) wears out and gets dirty during use so that when being detachable, it is easier to clean and be replaced with a new one and in case there are different paddings (15) to choose from, the appearance of the apparatus can be personified as one happens at a given time wish.

Figure 6:
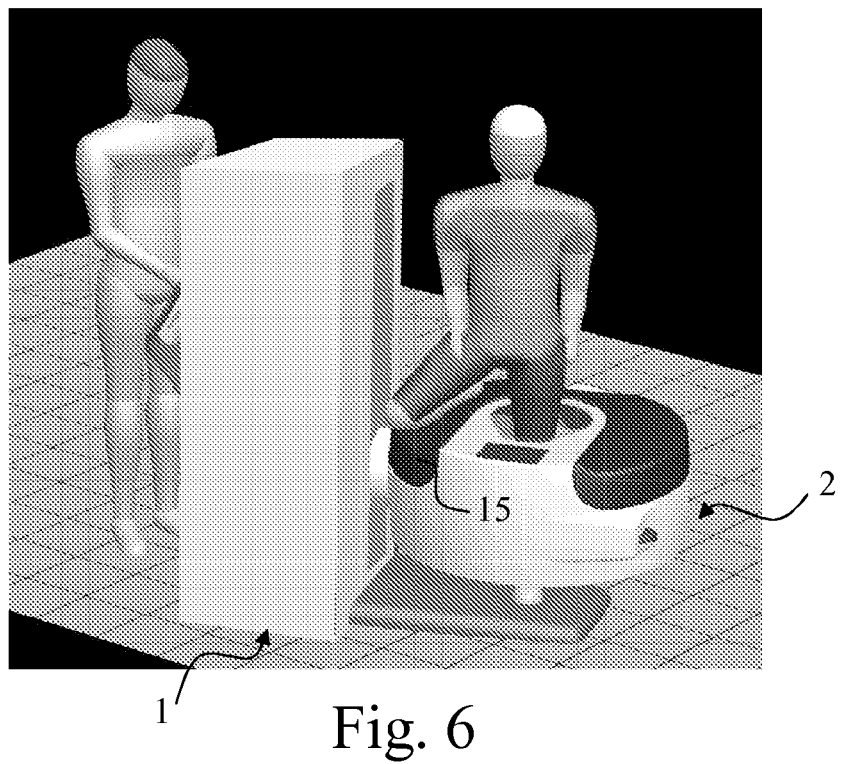
FIGS. 6 and 7 show the patient's posture at the imaging apparatus in connection with two different imaging situations.
Figure 7:
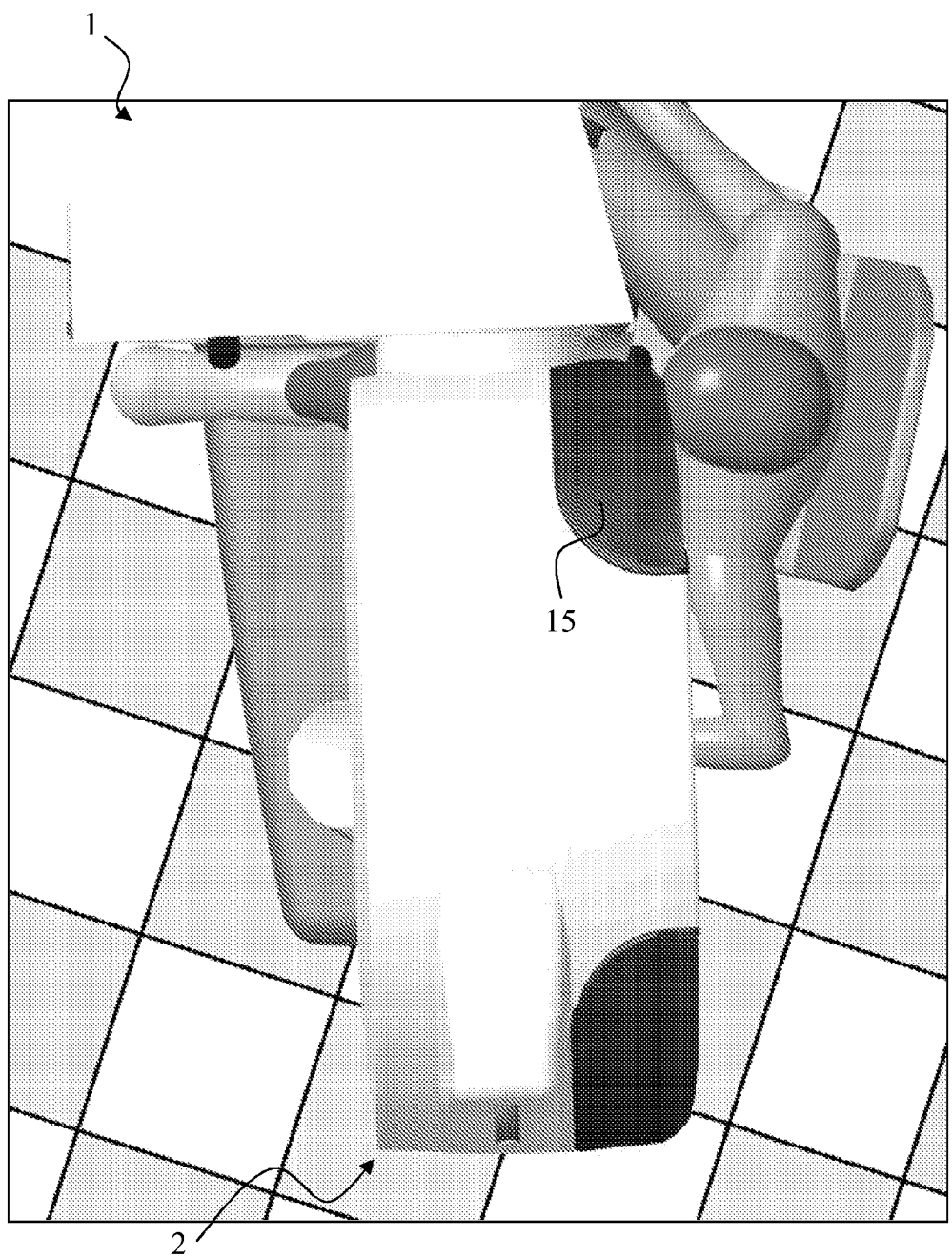

Using the padding improves patient comfort by offering a more pleasant surface for touch and support, which is nice to available considering the different operational states of the apparatus. It is preferable to arrange the padding (15) specifically on the area of the surface of the support structure (2) supporting the imaging means (21, 22), as in connection with several of the imaging modes the apparatus according to the invention offers, it is specifically that surface from where the patient can look for support in order to better remain stationary during an exposure, which lasts a considerable time. In FIG. 6, one leg of the patient is being imaged at a standing position, whereupon the padding (15) according to the invention offers a comfortable knee-support for the other leg to facilitate standing still. In FIG. 7, on the other hand, the patient's arm is being imaged and as a consequence, the patient is in a slightly awkward position but, remaining in that posture is substantially facilitated by the fact that the patient can lean on to the supportive padding (15) with his/her shoulder and/or head.

According to one preferable embodiment of the invention, the range of movement of the imaging means is implemented unlike in some prior-art apparatuses of similar type, i.e. by arranging the source of radiation (21) and the receiver of image information (22) movable along a curved path substantially on opposite sides of the examination opening (4) for a shorter distance than 360 degrees. This distance is referred to in the context of this specification as an angle of rotation, and preferably it is arranged to be somewhat larger than 180 degrees but then substantially smaller than 360 degrees, such as of the order of 210+/−20 degrees. Then, arranging the imaging means (21, 22) to be movable at different distances from the centre of rotation may preferably be implemented particularly in an arrangement comprising the above-described cut in the O-arm (2) and extension in the examination opening (4). The range of manoeuvring of the source of radiation (21) can be arranged not to extend to that sector of the O-arm in which the outer cover (3) has been cut like described above and, on the other hand, the range of manoeuvring of the receiver of image information (22) not to extend to that sector of the O-arm (2) in which is arranged an extension of the examination opening (4) as described above. When the utmost dimensions of said extension and cut from the centre of rotation of the imaging means are arranged appropriate with respect to those different distances at which the imaging means are rotated from the centre of rotation, the apparatus can be implemented as shown in FIG. 3 such that the source of radiation (21) arranged to move farther from the centre of rotation is able to move outside the extension of the examination opening (4) and the receiver of image information (22), again, inside the cut arranged to the outer cover (3) of the O-arm (2).

Especially, such embodiment of the invention enables a structure where, e.g. considering imaging of extremities, due to the extension arranged to the examination opening (4) it is possible to implement the diameter of the circular portion of the examination opening (4) smaller than would be possible without the extension sector and, further, it is possible to arrange the cut to the outer cover (3) of the O-arm (2) which facilitates several positioning procedures of a patient. Such an embodiment of the invention is implementable as a compact structure and it enables realizing both the examination opening (4) and the outer dimensions of the whole O-arm (2) smaller than would otherwise be possible.

It was mentioned above that the extension arranged to the examination opening (4) facilitates e.g. positioning of a plastered leg to the examination opening. Placing the anatomy to be imaged to the examination opening (4) can be further facilitated by arranging the patient positioning support (8) arranged in connection with the examination opening (4) movable or detachably attached such that it is both positionable to a desired location within the examination opening (4) for imaging and positionable or transferrable to a place where it impedes patient positioning as little as possible. The purpose of such patient positioning support (8) is to assist positioning of the anatomy being imaged to a desired point with respect to the O-arm (2). Preferably, the patient positioning support (8) comprises a concave structure whereto an upper or a lower extremity can be positioned for the duration of the imaging.

The angle of rotation of the imaging means (21, 22) described above is sufficient in cone-beam tomography, in which the beam generated by the source of radiation (21) is arranged to be limited to a true two-dimensional beam and the receiver of image information (22), again, of its form and dimensions at least such that it covers said two-dimensional beam. In the apparatus according to the invention, such beam can also be arranged to be limited to more than one size and/or shape, whereby the receiver of image information (22) must naturally be arranged either to cover all possible beam sizes and shapes or it must be arranged changeable.

The patient support rail (5) of the imaging apparatus shown in FIG. 1 is preferably arranged to extend from top of the support construction (1) substantially to at least one side of the support construction, especially to a side from the direction of which the patient is at least primarily thought to station oneself for imaging—i.e. preferably to the side in the direction of which the cut of the outer cover (3) of the O-arm (2) is arranged to be turned. The patient support rail (5) especially facilitates imaging in standing position, i.e. imagings where the O-arm (2) is turned into a position where its central axis is in the vertical orientation, when the patient can take support for himself/herself from the rail (5) when standing inside the O-arm (2) as well as when stepping in and out of it. In a preferable embodiment of the invention, the patient support rail (5) extends to at least one such side of the support construction (1) in the direction of which the cut sector arranged to the O-arm (2) is arranged to be turned.

The preferable embodiment of the invention described above can be implemented as a relatively compact structure and, for achieving many of the advantages described above, as a structure where the radius of the prevailing portion of the examination opening (4) being of the shape of an arch of a circle is of the order of 15 cm or slightly more and, on the other hand, the radius of the prevailing portion of the O-arm (2) of the shape of an arch of a circle is of the order of 50 cm or even less. Here, the distance of the focus of the source of radiation (21) from the centre of rotation of the imaging means (21, 22) can preferably be arranged e.g. for about 390 mm and that of the receiver of image information for about 190 mm. Since the apparatus is designed to enable imaging of extremities in several different positions, it means in practice that there are several ways to bring an extremity to the imaging area, and to position oneself to be imaged. The ways according to the invention and its preferable embodiments to arrange the padding to the apparatus assist in realizing a successful imaging event when facilitating keeping especially the anatomy to be imaged stationary during an exposure.

It is obvious for one skilled in the art that as for its details, the present invention may be implemented also in other ways than according to the embodiments of the invention described above.

The invention claimed is:

1. A medical computed tomography imaging apparatus for imaging extremities, which apparatus includes
   a support construction which is arranged to support a substantially ring-shaped structure supporting imaging means, which imaging means include a source of radiation and a receiver of image information, which imaging means are arranged within said substantially ring-shaped structure supporting the imaging means substantially on opposite sides of each other and movable within said ring-shaped structure supporting the imaging means,
   which apparatus includes in said ring-shaped structure supporting the imaging means an examination opening wherein the object to be imaged is positionable for imaging,
   and in which apparatus said substantially ring-shaped structure supporting the imaging means is arranged movable with respect to said support construction at least in the vertical direction and, on the other hand, turnable with respect to an axis substantially parallel with the horizontal diagonal of a radial cross-section of the ring-shaped structure in question,
   wherein at least one padding element is attached to said ring-shaped structure of the apparatus such that the patient can, depending on the imaging mode in question touch, lean on, kneel on, sit on or step on said at least one padding element when positioning oneself to be imaged, in connection with the actual patient positioning and/or during the actual imaging.

2. An imaging apparatus according to claim 1, wherein said at least one padding element is arranged to cover substantially entirely that surface of the structure supporting the imaging means from the direction of which the patient steps in or positions oneself to be imaged inside said ring-shaped structure supporting the imaging means.

3. An imaging apparatus according to claim 1, wherein said at least one padding element is arranged to cover that surface of the structure supporting the imaging means from the direction of which the patient steps in or positions oneself to be imaged inside said ring-shaped structure supporting the imaging means otherwise entirely but, considering the structure supporting the imaging means at its vertical position, an area is arranged within the upper section of that surface where there is no padding.

4. An imaging apparatus according to claim 3, wherein an area with no padding is arranged also at the lower portion of said surface.

5. An imaging apparatus according to claim 1, wherein at least one padding element is arranged on the surface of the support construction of the apparatus the normal of which points towards the structure supporting the imaging means.

6. An imaging apparatus according to claim 1, wherein said at least one padding element is arranged to the apparatus as detachably attached.

7. An imaging apparatus according to claim 1, wherein an area is arranged within said surface of the ring-shaped structure supporting the imaging means without the padding, and within said area without the padding is arranged a display screen.

8. An imaging apparatus according to claim 1, wherein said source of radiation and receiver of image information are arranged movable within said substantially ring-shaped structure supporting the imaging means with respect to a center of rotation for an angle of rotation which is wider than 180 degrees but narrower than 360 degrees.

9. An imaging apparatus according to claim 1, wherein said source of radiation and receiver of image information are arranged movable within said substantially ring-shaped structure supporting the imaging means with respect to a center of rotation such that the source of radiation moves at a different distance from said center of rotation than the receiver of image information.

10. An imaging apparatus according to claim 1, wherein within said ring-shaped structure supporting the imaging means is arranged a substantially ring-shaped support part, said source of radiation and receiver of image information are attached to that support part and said support part is arranged rotatable within the structure supporting the imaging means.

11. An imaging apparatus according to claim 1, wherein a beam generated by said source of radiation is arranged to be limited to a true two-dimensional beam and, again, the receiver of image information for its form and dimensions at least such that it covers said two-dimensional beam.

12. An imaging apparatus according to claim 1, wherein the radius of the prevailing portion of said examination opening which is substantially of the shape of an arch of a circle is of the order of 15 cm or somewhat more, the radius of the prevailing portion of said structure supporting the imaging means which is substantially of the shape of an arch of a circle is of the order of 50 cm or less, and/or that the distance of the focus of the source of radiation from the center of rotation of the imaging means is about 390 mm and the distance of the receiver of image information from the center of rotation of the imaging means is about 190 mm.

13. An imaging apparatus according to claim 1, wherein said source of radiation and receiver of image information are arranged movable within said substantially ring-shaped structure supporting the imaging means with respect to a center of rotation for an angle of rotation which is wider than 180 degrees and narrower than 230 degrees.

14. An imaging apparatus according to claim 1, wherein said source of radiation and receiver of image information are arranged movable within said substantially ring-shaped structure supporting the imaging means with respect to a center of rotation for an angle of rotation which is wider than 180 degrees and narrower than 190 degrees.

* * * * *